(12) United States Patent
Fowler et al.

(10) Patent No.: US 7,949,401 B2
(45) Date of Patent: May 24, 2011

(54) ELECTROMAGNETIC SIGNAL DELIVERY FOR TISSUE AFFECTED BY NEURONAL DYSFUNCTION, DEGRADATION, DAMAGE, AND/OR NECROSIS, AND ASSOCIATED SYSTEMS AND METHODS

(75) Inventors: Brad Fowler, Duvall, WA (US); Bradford E. Gliner, Sammamish, WA (US); David Himes, Seattle, WA (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 865 days.

(21) Appl. No.: 11/697,694

(22) Filed: Apr. 6, 2007

(65) Prior Publication Data

US 2008/0039895 A1 Feb. 14, 2008

Related U.S. Application Data

(60) Provisional application No. 60/790,868, filed on Apr. 11, 2006.

(51) Int. Cl.
*A61N 1/36* (2006.01)
(52) U.S. Cl. ......... 607/45; 607/1; 607/2; 600/9; 600/13; 600/544
(58) Field of Classification Search ................ 600/9, 13, 600/544; 607/1–2, 45
See application file for complete search history.

(56) References Cited

U.S. PATENT DOCUMENTS

| | | | |
|---|---|---|---|
| 6,463,328 | B1 | 10/2002 | John |
| 2004/0088024 | A1 | 5/2004 | Firlik et al. |
| 2004/0138550 | A1 | 7/2004 | Hartlep et al. |
| 2006/0015153 | A1 | 1/2006 | Gliner et al. |

OTHER PUBLICATIONS

International Search Report and Written Opinion for PCT/US2007/66220; Applicant: Northstar Neuroscience, Inc.; dated Apr. 18, 2008; 13 pgs.

*Primary Examiner* — Carl H Layno
*Assistant Examiner* — Deborah Malamud
(74) *Attorney, Agent, or Firm* — Melissa Acosta; Christopher S. L. Crawford; Craig Hoersten (57) ABSTRACT

Electromagnetic signal delivery for tissue affected by neuronal dysfunction, degradation, damage, and/or necrosis, and associated systems and methods are disclosed. A method in accordance with one embodiment of the invention includes identifying an affected region, with the affected region including neuronal tissue that, at least during a pre-dysfunctional period, was in neural communication with neuronal tissue in a dysfunctional region. The affected tissue can be functionally adversely affected by neuronal dysfunction in the dysfunctional region. The method can further include applying electromagnetic signals to the neuronal tissue in the affected region. For example, the electromagnetic signals can be applied to a hypo-active neural region that is not physically damaged, and has been identified as likely to recover at least in part as a result of electromagnetic signals. Signals can be applied at sub-threshold levels to cortical and/or subcortical regions.

13 Claims, 8 Drawing Sheets

ELECTROMAGNETIC SIGNAL DELIVERY FOR TISSUE AFFECTED BY NEURONAL DYSFUNCTION, DEGRADATION, DAMAGE, AND/OR NECROSIS, AND ASSOCIATED SYSTEMS AND METHODS

CROSS-REFERENCE TO RELATED APPLICATION

The present application claims priority to U.S. Provisional Application No. 60/790,868, filed Apr. 11, 2006, and incorporated herein by reference.

TECHNICAL FIELD

The present disclosure is directed generally toward electromagnetic signals applied to neuroanatomical regions affected by neuronal dysfunction, degradation, damage, and/or necrosis (e.g., arising in association with an infarct and/or another condition), and associated systems and methods.

BACKGROUND

A wide variety of mental and physical processes are controlled or influenced by neural activity in particular regions of the brain. In some areas of the brain, such as in the sensory or motor cortices, the organization of the brain resembles a map of the human body; this is referred to as the "somatotopic organization of the brain." There are several other areas of the brain that appear to have distinct functions that are located in specific regions of the brain in most individuals. For example, areas of the occipital lobes relate to vision, regions of the left inferior frontal lobes relate to language in the majority of people, and regions of the cerebral cortex appear to be consistently involved with conscious awareness, memory, and intellect. This type of location-specific functional organization of the brain, in which discrete locations of the brain are statistically likely to control particular mental or physical functions in normal individuals, is herein referred to as the "functional organization of the brain."

Many problems or abnormalities with body functions can be caused by damage, disease and/or disorders of the brain. A stroke, for example, is one very common condition that damages the brain. Strokes are generally caused by emboli (e.g., obstruction of a vessel), hemorrhages (e.g., rupture of a vessel), or thrombi (e.g., clotting) in the vascular system of a specific region of the cortex, which in turn generally causes a loss or impairment of a neural function (e.g., neural functions related to face muscles, limbs, speech, etc.). Stroke patients are typically treated using physical therapy to rehabilitate the loss of function of a limb or another affected body part. For most patients, little can be done to improve the function of the affected limb beyond the recovery that occurs naturally without intervention.

One existing physical therapy technique for treating stroke patients constrains or restrains the use of a working body part of the patient to force the patient to use the affected body part. For example, the loss of use of a limb is treated by restraining the other limb. Although this type of physical therapy has shown some experimental efficacy, it is expensive, time-consuming and little-used. Stroke patients can also be treated using physical therapy and/or drug therapies. For example, some types of drugs, including amphetamines, increase the activation of neurons in general. However, these drugs may have limited efficacy because they are very non-selective in their mechanisms of action and cannot be delivered in appropriate concentrations directly at the site where they are needed. Still another approach is to apply electrical stimulation to the brain to promote the recovery of functionality lost as a result of a stroke. While this approach has been generally effective, in some cases particular tissue characteristics may impact neural stimulation efficacy. Therefore, there is a need to develop more effective and efficient treatments for rehabilitating stroke patients and patients who have other types of neurologic dysfunction or damage.

DETAILED DESCRIPTION

A. Introduction

The present disclosure is directed generally toward systems and methods for stimulating tissue affected by neuronal dysfunction, degradation, damage, and/or necrosis, any of which may be generally referred to herein as neuronal damage and/or dysfunction. Such neuronal damage or dysfunction may arise, for example, in association with a cerebral infarct, neuronal trauma (e.g., associated with central nervous system injury), neurodegenerative disease (e.g., Alzheimer's disease or Multiple Sclerosis (MS)), or other conditions.

In at least some cases, the affected tissue will not be directly damaged (by lack of oxygen, lesion or otherwise), but would normally be in direct or indirect electrical and/or chemical communication with tissue that has been damaged. It is believed that in at least some cases, otherwise healthy neural tissue may suffer and perhaps die as a result of a reduction or loss in communication with formerly active tissue within a dysfunctional region. Accordingly, a method in accordance with at least one aspect of the invention includes identifying an affected region having neuronal tissue that, at least during a pre-damage or pre-degradation period, was in neural communication with neuronal tissue in a presently damaged or dysfunctional region. The neuronal tissue in the affected region includes neuronal tissue that is functionally adversely affected by neuronal dysfunction in the dysfunctional region. In particular embodiments, the neuronal tissue in the affected region is not initially physically or structurally damaged, though over the course of time, it may become damaged. In some embodiments, an affected region may include impaired tissue having at least some likelihood of surviving, as further detailed below. The method can further include applying electromagnetic signals to the neuronal tissue in the affected region, which can delay or prevent the physical or structural damage to this tissue.

In further specific aspects of the invention, the method can include identifying and applying electromagnetic signals to one or more affected regions that may be likely to recover and/or facilitate development of compensatory function, at least in part, in association with the application of electromagnetic signals. Other regions, which may be unlikely or less likely to benefit from electromagnetic signals, may not receive such signals. Applying electromagnetic signals can include applying electromagnetic signals to neuronal structures or regions that include neurons, viable projections, viable tracts, or some combination of these. Such projections and/or tracts may correspond to communication pathways to and/or from a damaged or otherwise dysfunctional region, another affected region, and/or other neural tissues.

In general, a dysfunctional region and/or an affected region may reside within any portion of an individual's central nervous system. Depending upon an individual's neurologic condition and/or embodiment details, a dysfunctional and/or an affected region may include portions of a patient's cerebral cortex, particular subcortical and/or deep brain structures, one or more cerebellar regions, and/or portions of the patient's spinal cord. For example, in some cases, a dysfunctional region can include a cortical, subcortical, and/or deep brain structure, and an affected region can be at least proximate to a cortical region of the patient's brain; or the affected region can be a deep brain or other subcortical region. As another example, a dysfunctional region can include a portion of the spinal cord, while an affected region may include a cortical region, a subcortical or deep brain region, and/or another portion of the spinal cord.

Various techniques can be used to identify a dysfunctional and/or an affected region, including neural imaging techniques such as Magnetic Resonance Imaging (MRI), functional MRI (fMRI), diffusion tensor imaging (DTI), Magnetic Resonance Spectroscopy (MRS), and/or perfusion weighted or diffusion weighted imaging (PWI or DWI). The type(s) of treatment administered at different stages, phases, periods, or times in view of the patient's neurologic condition may also differ. In several embodiments, during a first treatment phase, applied electromagnetic signals may be directed toward providing, enhancing, or maintaining a particular level of neural communication with one or more affected regions. During a second treatment phase, applied signals may be directed toward facilitating neural communication that (a) reinforces or enhances existing neurofunctional capabilities, and/or (b) develops new neurofunctional capabilities. Particular adjunctive therapies (e.g., a chemical substance therapy (including, but not limited to, Botox therapy to reduce patient symptoms associated with hypertonicity or spasticity) and/or a behavioral therapy) may be applied to the patient in association with the neural signals, possibly depending upon the patient's neurologic condition during one or more portions of a given treatment phase.

In one embodiment directed toward treating neuronal dysfunction arising from an infarct or injury, the patient may possibly undergo a first type of adjunctive therapy during a post-acute, pre-chronic phase, and the adjunctive therapy may be discontinued as the patient enters a chronic phase. The patient may alternatively or subsequently undergo a second type of adjunctive therapy during the chronic phase. In still further embodiments, a method can include preferentially stimulating first neuronal regions or cells having a hypoactive and/or generally normal spontaneous electrical activity level, and avoiding or attempting to avoid the stimulation of second neuronal regions or cells having a hyperactive spontaneous electrical activity level. In yet another embodiment, the second neuronal cells can be exposed to inhibitory electrical signals that reduce the activity levels of these cells. In the event that the spontaneous electrical activity levels of the second neuronal cells become generally normal or hypoactive, the method can further include stimulating the second neuronal cells. Accordingly, aspects of the method can include (a) initially targeting hypoactive neuronal cells, which may require and/or benefit from excitatory or facilitatory signals more than other neuronal cells that may be present, and then (b) applying excitatory or facilitatory signals to the initially hyperactive neuronal cells only after the level of hyperactivity has declined.

Figure 1:
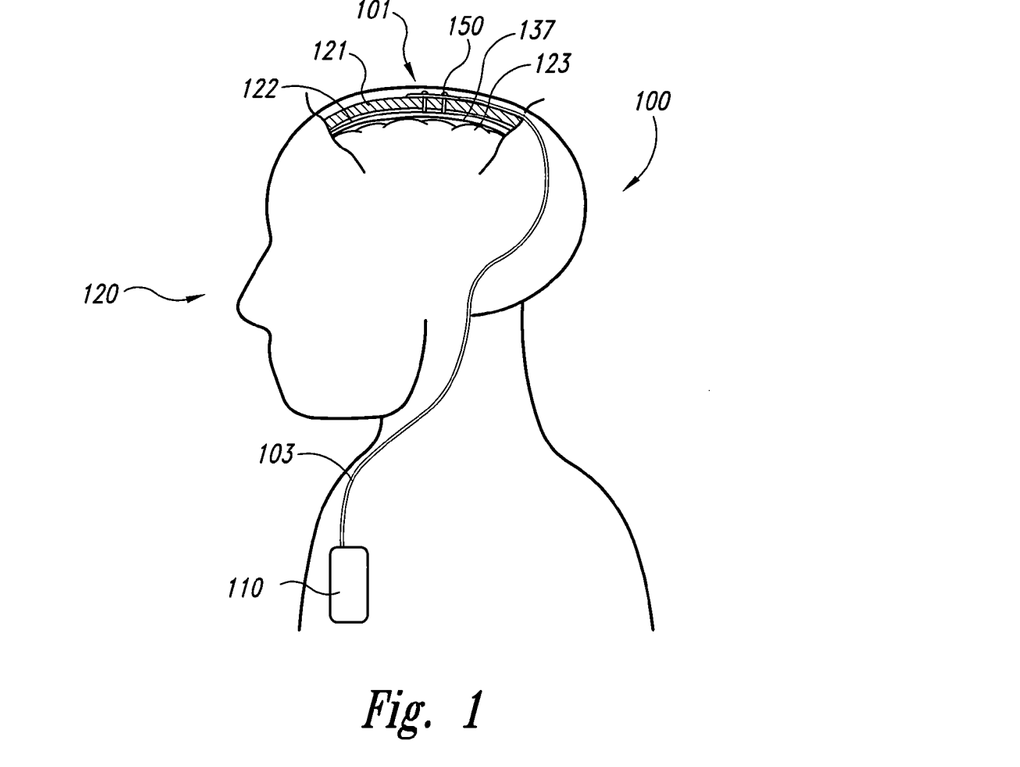
FIG. 1 is a partially schematic, left side illustration of a human brain and an implanted neurostimulation system positioned to provide electromagnetic signals in accordance with an embodiment of the invention.

B. Selection of Signal Delivery Sites and General Characteristics of Signal Delivery Devices FIG. 1 is a schematic illustration of a signal delivery system 100 implanted in a patient 120 to provide electromagnetic signals in accordance with several embodiments of the invention. The signals can be directed to tissue that is not structurally damaged, but may be adversely affected by a proximate infarct. The system 100 can include one or more signal delivery devices 101 (e.g., an electrode device) carrying one or more electrodes 150 or other signal delivery elements. A representative signal delivery device 101 can be positioned in the skull 121 of the patient 120, with the electrodes 150 positioned to direct signals to target areas of the brain 123. For example, the electrodes 150 can be positioned just outside the dura mater 122 (which surrounds the brain 123) to direct signals to cortical tissue. In other embodiments described later with reference to FIGS. 8 and 9, the electrodes 150 can penetrate the dura mater 122 to direct signals to subcortical tissues. In still further embodiments, the electrodes 150 can penetrate the dura mater 122 but not the underlying pia mater 137, and can accordingly provide signals through the pia mater 137.

The signal delivery device 101 can be coupled to a pulse system 110 with a communication link 103. The communication link 103 can include one or more leads, depending upon the number of electrodes 150 carried by the signal delivery device 101. The pulse system 110 can direct electromagnetic signals to the signal delivery device 101 for delivery to target neural tissues. The pulse system 110 may be an implantable pulse generator (IPG), or an implantable microstimulation device such as a BION™ (Advanced Bionics, Sylmar, Calif.). In other embodiments, other types of signal delivery devices (e.g., rTMS devices or tDCS devices) can be used to treat the target neural tissues. Several embodiments for selecting the target neural tissues and applying signals to the target neural tissues as part of a treatment regimen are described below.

Figure 2:
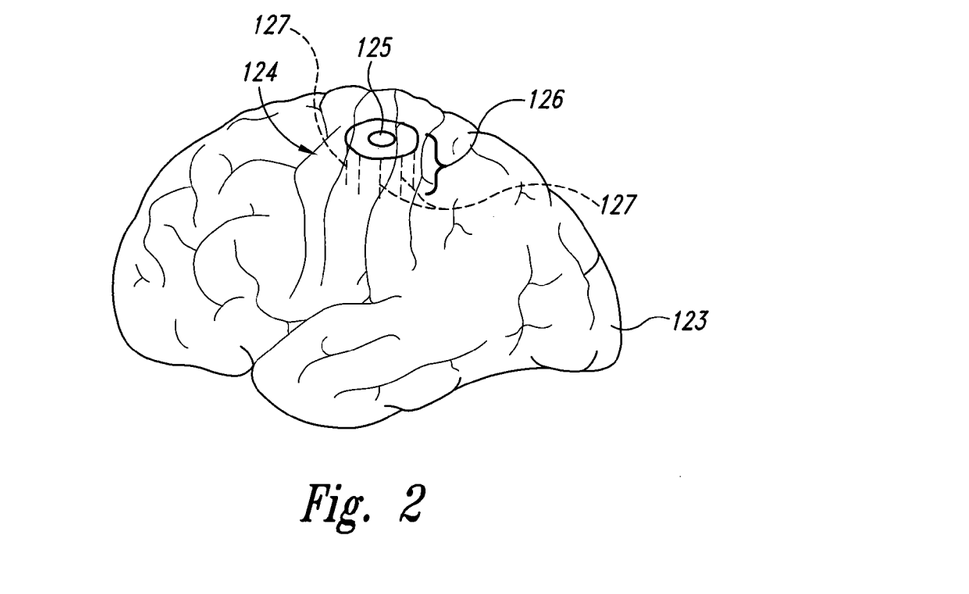
FIG. 2 is a partially schematic, isometric view of the brain, illustrating a dysfunctional region and an affected region.

FIG. 2 is a side isometric illustration of the brain 123, illustrating a lesion area 124. The lesion area 124 can include a dysfunctional region 125 and an affected region 126 positioned generally adjacent to the dysfunctional region 125. The dysfunctional region 125 can include neural tissue that has been physically damaged or degraded, or has otherwise suffered a loss in functionality, for example, by a stroke, a trauma, or another ischemic or non-ischemic event. For example, the dysfunctional region 125 can include an infarct region. The affected region 126 can include neural tissue that communicated with the dysfunctional region 125 prior to the presence of the dysfunction, and that is functionally adversely affected by dysfunction in the dysfunctional region 125. For example, the affected region 126 may have communicated with the dysfunctional region 125 via projections 127 (shown schematically in the Figures). The projections 127 can include tracts (e.g., nerve bundles) or other neuronal pathways via which neural signals can be transmitted. As described in greater detail below, the decrease and/or loss of such communication can be mitigated in part or in whole by properly directed electromagnetic signals.

As shown in FIG. 2, the affected region 126 is generally in the same brain hemisphere as the dysfunctional region 125. Accordingly, the communication (or former communication) between the dysfunctional region 125 and the affected region 126 is generally not transcollosal. In other embodiments, the affected region 126 may be in the opposite brain hemisphere from the dysfunctional region 125, and the communication between the two regions may be transcollosal. Depending upon the particular patient condition, the brain 123 may have multiple affected regions in one or both hemispheres.

Figure 3:
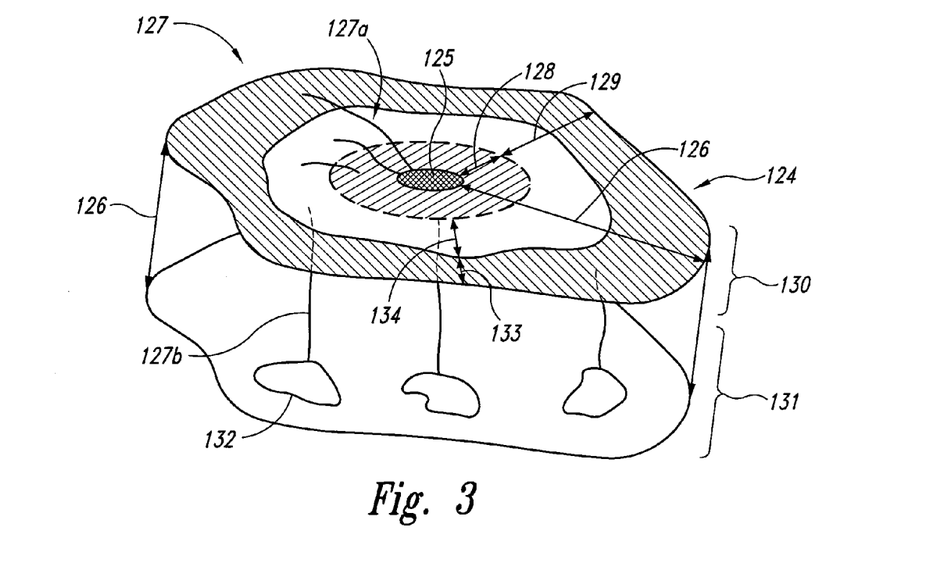
FIG. 3 is a partially schematic, enlarged view of the dysfunctional region and the affected region shown in FIG. 2.

FIG. 3 is a schematic, enlarged isometric illustration of the lesion area 124 and surrounding tissue shown in FIG. 2. Representative structures and relative positions between those structures are shown schematically in FIG. 3 for purposes of illustration. It will be understood by those of ordinary skill in the relevant art that such structures may have other arrangements and/or relative positions in other embodiments. As shown in FIG. 3, the affected region 126 can extend away from the dysfunctional region 125 in multiple directions. For example, the affected region 126 can extend laterally away from the dysfunctional region 125 within a cortical region 130 of the brain 123. The affected region 126 can also extend inwardly to a subcortical region 131 of the brain 123. Accordingly, the projections 127 between the affected region 126 and the dysfunctional region 125 can include cortical projections 127a that extend between the dysfunctional region 125 and cortical structures. The projections 127 can also include subcortical projections 127b that extend between subcortical structures 132 (located in the subcortical region 131) and the dysfunctional region 125, as well as between the subcortical structures 132 and cortical portions of the affected region 126.

In at least some embodiments, those portions of affected region 126 that are to receive electromagnetic signals may be readily identified simply as the regions that are proximate to (e.g., adjacent to) the dysfunctional region 125. Accordingly, these regions can be determined based on general anatomical principles. In other embodiments, the target areas can be identified by locating or estimating the location(s) of particular neural projections 127 that extend to or from a dysfunctional region 125, an affected region 126, and/or other brain areas involved in controlling a neural function that was subserved by the dysfunctional or affected regions 125, 126. By using this technique, the practitioner can identify tissue that communicated with the dysfunctional region 125 prior to the presence of the dysfunction, and that may be functionally degraded as a result of the loss of communication with the dysfunctional region 125.

In some embodiments, the tracts can be identified by reference to known brain structures. For example, the peduncle of the brain (a deep brain structure located just above the brain stem), somatotopically maps to the cortex via neural projections or tracts. Accordingly, one approach toward treating neurologic dysfunction associated with damaged or affected regions 125, 126 in the cortex involves applying deep brain stimulation to or near particular portions of the peduncle based upon peduncular somatotopy. Alternatively or additionally, other brain areas (e.g., portions of the cortex such as an affected region 126 expected to have at least some intact peduncular projections) may be stimulated. In particular embodiments, tractography techniques, including diffusion tensor imaging techniques, can be used to identify the locations and/or densities of particular projections or other tracts between brain regions, such as portions of the peduncle and portions of the cortex. Such techniques are described by Lazar et al. in "White Matter Tractography Using Diffusion Tensor Deflection" (Human Brain Mapping 18:206-321 (2003)). Diffusion tensor MRI uses a measured diffusion of water in brain tissue to identify neuronal fibers and tracts, by relying on the observation that such diffusion is generally greater along the tracts than transverse to the tracts. The brain tissue can be computationally broken down into a series of voxels with pathways constructed on a voxel-by-voxel basis using an estimate of tract direction at each voxel. The diffusion tensor defines the principle frame of direction to each voxel by its eigenvectors. The connectivity between regions of the brain can be estimated using a variety of techniques, including streamlined tracking and tensor deflection. These techniques, when combined with computer aided imaging, can identify to the practitioner the tracts or nerve bundles that connect neural regions and provide communication pathways between such regions. Suitable software for analyzing and displaying diffusion tensors is available at http://software.sci.utah.edu/scirun.html and http://www.fmrib.ox.ac.uk/fsh/. The projections, tracts, and/or nerve bundles between a dysfunctional region 125, an affected region 126, and/or particular central nervous system structures (e.g., peduncular, basal ganglia, or thalamic locations) can be traced to identify one or more portions of an affected region 126 that may benefit from receiving electromagnetic signals. The foregoing and/or other neural tractography techniques can be used not only to identify tracts, but to assess the viability or density of the tracts.

An affected region 126 can include high morbidity tissue 128 and low morbidity tissue 129. As used herein, the term high morbidity tissue 128 refers generally to tissue that is unlikely to survive (e.g., has less than a 50% likelihood for survival), typically as a result of the damage sustained by the dysfunctional region 125. Low morbidity tissue 129 refers generally to tissue that has a relatively high likelihood of survival (e.g., greater than 50%). In at least some of these embodiments, the high morbidity tissue 128 tends to be located closer to the dysfunctional region 125 than does the low morbidity tissue 129. A method in accordance with one aspect of the invention includes identifying the low morbidity tissue 129 and applying electromagnetic signals with greater preference for the low morbidity tissue 129 than for the high morbidity tissue 128. Any one or more of several available techniques can be used to distinguish the high morbidity tissue 128 from the low morbidity tissue 129. Such techniques can include magnetic resonance imaging techniques based on diffusion and/or perfusion imaging. In particular embodiments, relative cerebral blood flow (which may be measured, calculated, or estimated in a variety of manners, including optically) can be used to distinguish these regions. Further details of such techniques are disclosed by Schaefer et al. ("Assessing Tissue Viability With MR Diffusion And Perfusion Imaging," AJNR Am. J. Neuroradiol 24: 436-433, March 2003), incorporated herein by reference.

The affected region 126 can also include a hypoactive region 134 and a hyperactive region 133. The hypoactive region 134 includes neuronal cells having a spontaneous electrical activity level that is below that of normal neuronal cells. The hyperactive region 133 includes neuronal cells having a spontaneous electrical activity level that is above that of normal neuronal cells. The hypoactive and hyperactive regions 134, 133 can be distinguished from each other using known techniques. Such techniques include using the signal delivery electrodes of an implanted neurostimulation device (e.g., the device 101 shown in FIG. 1) as sensing electrodes in an electrocortocography or ECoG manner. Other suitable techniques include using EEG electrodes on the patient's scalp, PET methods, and/or using a magnetic imaging or perfusion-weighted imaging technique. Suitable EEG systems (e.g., a GES 250 system) are available from Electrical Geodesics, Inc. of Eugene, Oreg.

Once the hypoactive and hyperactive regions 134, 133 and possibly normal or generally normal regions are distinguished from each other, it may be advantageous to preferentially apply excitatory signals to the hypoactive region 134 and provide less or no excitatory signals to the hyperactive region 133, or provide inhibitory signals to the hyperactive region 133. Over the course of time and as a result of a therapy program that includes neural stimulation, the hypoactive region 134 may become less hypoactive, and the hyperactive region 133 may become less hyperactive. Accordingly, excitatory signals may be applied to the hyperactive region 133 after the activity level in this region decreases. Excitatory signals may be reduced for the hypoactive region 134 as the neural activity level in this area increases. Techniques that are the same as or generally similar to those described above in the context of distinguishing between hypoactive areas and hyperactive areas, can also be used to determine when the neural activities in these areas change.

Visualization techniques can be used in still further contexts in other embodiments. For example, magnetic resonance spectroscopy (MRS) can be used to track changes in the size and/or location of the dysfunctional region 125 and/or the affected region 126. As these changes are detected, the manner in which signals are applied can be updated. In particular embodiments, different electrodes can be activated as the regions 125, 126 change size, shape and/or location. Suitable devices that include multiple electrodes are described in greater detail below with reference to FIG. 7.

Figure 4:
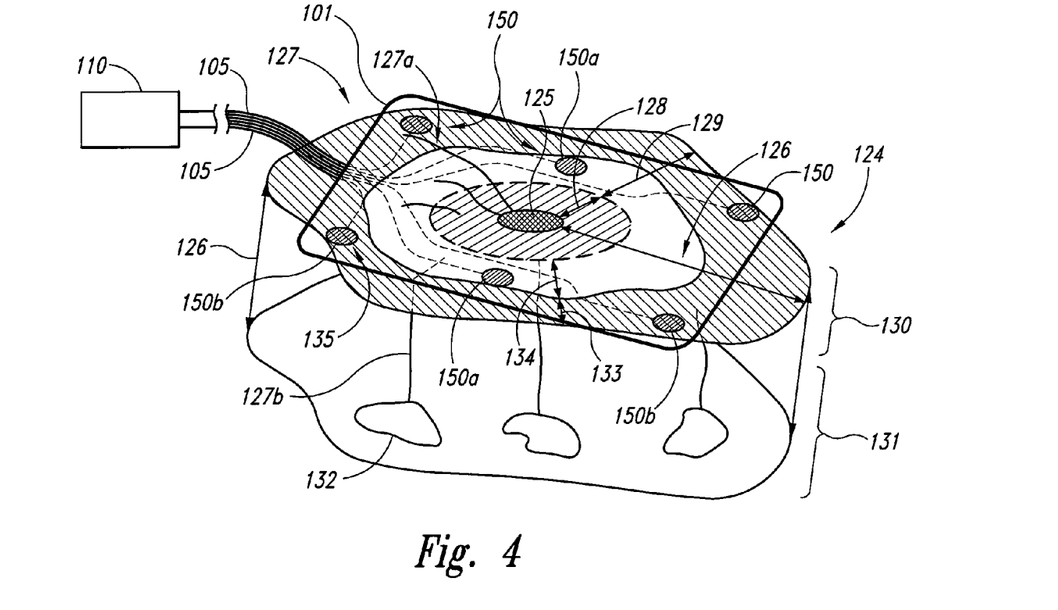
FIG. 4 illustrates an electromagnetic signal delivery device positioned proximate to a dysfunctional region in accordance with an embodiment of the invention.

FIG. 4 is a schematic illustration of an embodiment of a signal delivery device 101 implanted proximate to the lesion area 124. The signal delivery device 101 can include an array of electrodes 150 (including first electrodes 150a and second electrodes 150b), elements of which may be controlled separately and/or in groups to provide the desired signal to the desired target neural tissue. In an embodiment shown in FIG. 4, each electrode 150 can be coupled to the pulse system 110 via an individual lead 105. Accordingly, each electrode 150 can be individually activated or deactivated, depending on the location of a particular target signal delivery site 135.

In a particular embodiment, the signal delivery device 101 can be positioned over the lesion area 124 so that all the electrodes 150 are positioned in the low morbidity tissue region 129. In some cases, it may not be immediately apparent where the boundary between the low morbidity tissue 129 and the high morbidity tissue 128 lies. In such cases, the signal delivery device 101 can be positioned so that some electrodes 150 are positioned over a region that may or may not contain low morbidity tissue 129 (and may in fact include high morbidity tissue 128). If in fact this region turns out to contain low morbidity tissue 129, electrical signals can be provided via proximately placed electrodes 150 without moving the signal delivery device 101 or reimplanting a different signal delivery device 101.

The electrodes 150 can also be positioned proximate to both the hypoactive region 134 and the hyperactive region 133. For example, as shown in FIG. 4, first electrodes 150a can be positioned proximate to the hypoactive region 134, and second electrodes 150b can be positioned proximate to the hyperactive region 133. During an initial signal delivery period, the first electrodes 150a can be activated to direct signals to the hypoactive region 134. During a later stage of treatment (e.g., after tissue in the hyperactive region 133 reduces its activity level), the second electrodes 150b proximate to the formerly hyperactive region 133 can be activated. Alternatively, during portions of an initial signal delivery period, the first electrodes 150a can be activated to provide facilitatory stimulation to the hypoactive region 134 (e.g., by delivering electrical signals having a pulse repetition frequency of approximately 50-100 Hz), and the second electrodes 150b can be activated to provide inhibitory or disruptive stimulation to the hyper active region 133 (e.g., by delivering electrical signals at approximately 0.1-10 Hz, and/or delivering aperiodic signals). Optionally, the first electrodes 150a in the hypoactive region 134 can be deactivated if signals are no longer required in this region.

In a particular embodiment, the electrodes 150 can be activated and deactivated in a closed loop arrangement. Accordingly, the pulse system 110 can receive signals corresponding to the spontaneous electrical activity of the neuronal cells in the target region, and can direct the electromagnetic signals appropriately. For example, if a specific region changes from hyperactive to hypoactive, the system can automatically detect the change and activate (or deactivate) the appropriate electrode(s) in an appropriate manner. Signals corresponding to the spontaneous activity level of the neuronal cells can be provided via the electrodes 150 themselves (e.g., during a time period when the electrodes 150 are not actively delivering signals and instead act as sensors) and/or by other electrodes (e.g., scalp-mounted EEG electrodes).

The signals provided by the electrodes 150 can be unipolar or bipolar. For example, during unipolar signal delivery, the active electrodes 150 can be biased at a given electrical potential, and the implanted pulse system 110 can provide a current return path. During bipolar signal delivery, at least one of the electrodes 150 can provide the return path. For example, during bipolar signal delivery to the hypoactive region 134, one of the first electrodes 150a can be biased at an elevated potential and another of the first electrodes 150a can provide a current return path.

In an embodiment shown in FIG. 4, the signal delivery device 101 is positioned in the same hemisphere as the lesion area 124. In other embodiments, as identified above with reference to FIG. 2, one or more signal delivery devices 101 can be positioned at homologous and/or non-homologous sites in the contralesional hemisphere, in addition to or in lieu of placing one or more signal delivery devices at the ipsilesional hemisphere. Applying signals to the contralesional hemisphere can provide overall benefits and specific benefits for the ipsilesional tissues, at least in some instances by taking advantage of transcollosal connections between the hemispheres.

The intensity level of signals provided to the target site can be selected to be at subthreshold levels in at least some embodiments. As used herein, subthreshold signals refers to signals below a level that causes an inherent patient response or results in an inherent patient sensation. The threshold level can accordingly be identified as a threshold current and/or voltage. Signals can be provided at between 10% and 90% of threshold, for example, between about 25% and 75% of threshold. In some embodiments, the signals can be provided at low levels (e.g., 10%-25% of threshold) initially, and these levels can be increased over time. In some cases, signals can also be provided at suprathreshold levels.

Figure 5:
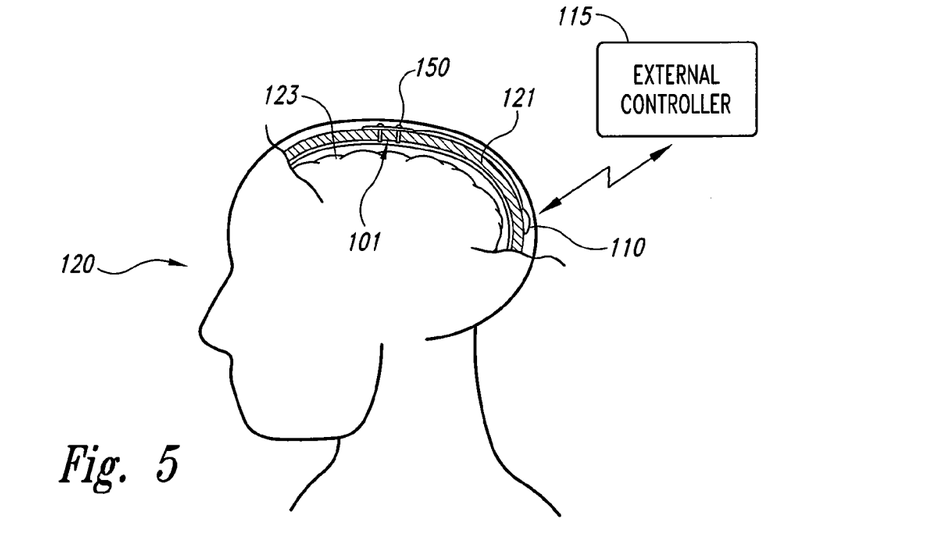
FIG. 5 illustrates a signal delivery device operatively coupled to an external controller in accordance with another embodiment of the invention.

The pulse system 110 shown in FIG. 4 can be implanted at a subclavicular location, as shown in FIG. 1. The pulse system 110 can also be controlled internally via pre-programmed instructions that allow the pulse system 110 to operate autonomously after implantation. In other embodiments, the pulse system 110 can be implanted at other locations, and at least some aspects of the pulse system 110 can be controlled externally. For example, FIG. 5 illustrates an embodiment of the system 100 in which the pulse system 110 is positioned on the external surface of the skull 121, beneath the scalp. The pulse system 110 can be controlled internally and/or via an external controller 115.

Figure 6:
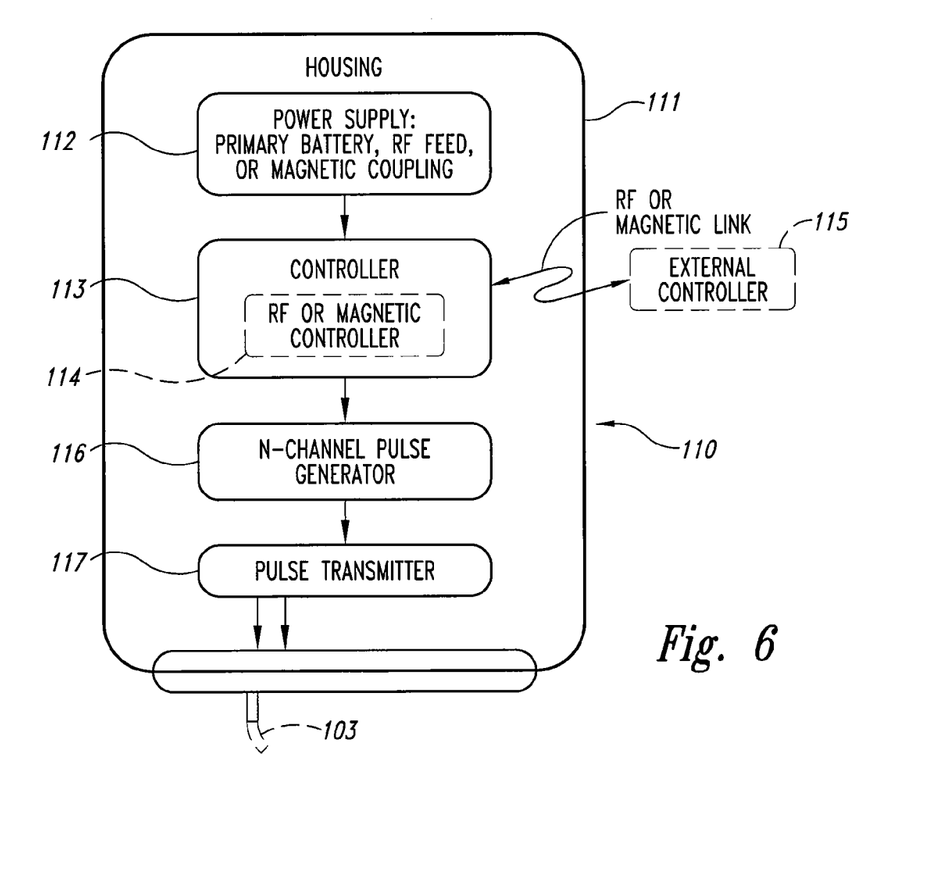
FIG. 6 is a schematic illustration of a pulse system configured in accordance with an embodiment of the invention.

FIG. 6 schematically illustrates one pulse system 110 suitable for use in the signal delivery system 100 described above. The pulse system 110 generally includes a housing 111 carrying a power supply 112, an integrated controller 113, a pulse generator 116, and a pulse transmitter 117. The power supply 112 can be a primary battery, such as a rechargeable battery or other suitable device for storing electrical energy. In other embodiments, the power supply 112 can be an RF transducer or a magnetic transducer that receives broadcast energy emitted from an external power source and that converts the broadcast energy into power for the electrical components of the pulse system 110.

In one embodiment, the integrated controller 113 can include a processor, a memory, and a programmable computer medium. The integrated controller 113, for example, can be a microcomputer, and the programmable computer medium can include software loaded into the memory of the computer, and/or hardware that performs the requisite control functions. In another embodiment identified by dashed lines in FIG. 6, the integrated controller 113 can include an integrated RF or magnetic controller 114 that communicates with the external controller 115 via an RF or magnetic link. In such an embodiment, many of the functions performed by the integrated controller 113 may be resident on the external controller 115 and the integrated portion 114 of the integrated controller 113 may include a wireless communication system.

The integrated controller 113 is operatively coupled to, and provides control signals to, the pulse generator 116, which may include a plurality of channels that send appropriate electrical pulses to the pulse transmitter 117. The pulse generator 116 may have multiple channels, with at least one channel associated with each of the electrodes 150 described above. The pulse generator 116 sends appropriate electrical pulses to the pulse transmitter 117, which is coupled to a plurality of the electrodes 150 (FIG. 4). In one embodiment, each of these electrodes 150 is configured to be physically connected to a separate lead, allowing each electrode 150 to communicate with the pulse generator 116 via a dedicated channel. Suitable components for the power supply 112, the integrated controller 113, the external controller 115, the pulse generator 116, and the pulse transmitter 117 are known to persons skilled in the art of implantable medical devices.

The pulse system 110 can be programmed and operated to adjust a wide variety of signal delivery parameters, for example, which electrodes are active and inactive, whether electrical signals are provided in a unipolar or bipolar manner, and/or how the signals are varied. In particular embodiments, the pulse system 110 can be used to control the polarity, frequency, pulse shape(s) and/or width(s), duty cycle, amplitude, temporal, and/or spatial and/or topographical qualities of the signals. The delivery of the signals can be varied to match naturally occurring burst patterns (e.g., theta burst patterns), and/or the signals can be varied in a predetermined, pseudorandom, and/or aperiodic manner at one or more times and/or locations. The pulse system may be implemented in one or more manners described in U.S. Pat. No. 7,010,351 or U.S. Application No. 2006/0015153, both of which are incorporated herein by reference.

A given treatment regimen may also include one or more adjunctive or synergistic therapies to facilitate enhanced symptomatic relief and/or at least partial recovery from neurological dysfunctions. An adjunctive or synergistic therapy may include a behavioral therapy, such as a physical therapy activity, a movement and/or balance exercise, an activity of daily living (ADL), a vision exercise, a reading exercise, a speech task, a memory or concentration task, a visualization or imagination exercise, an auditory activity, an olfactory activity, a relaxation activity, and/or another type of behavior, task or activity. In other embodiments, the adjunctive therapy can include the introduction of a drug or other chemical substance into the patient's body. In any of these embodiments, the relative timing between the electromagnetic signal delivery portion of the treatment regimen and the adjunctive therapy portion of the treatment regimen can be controlled and/or altered during the course of the treatment regimen.

C. Further Examples of Signal Delivery Devices

Figure 7:
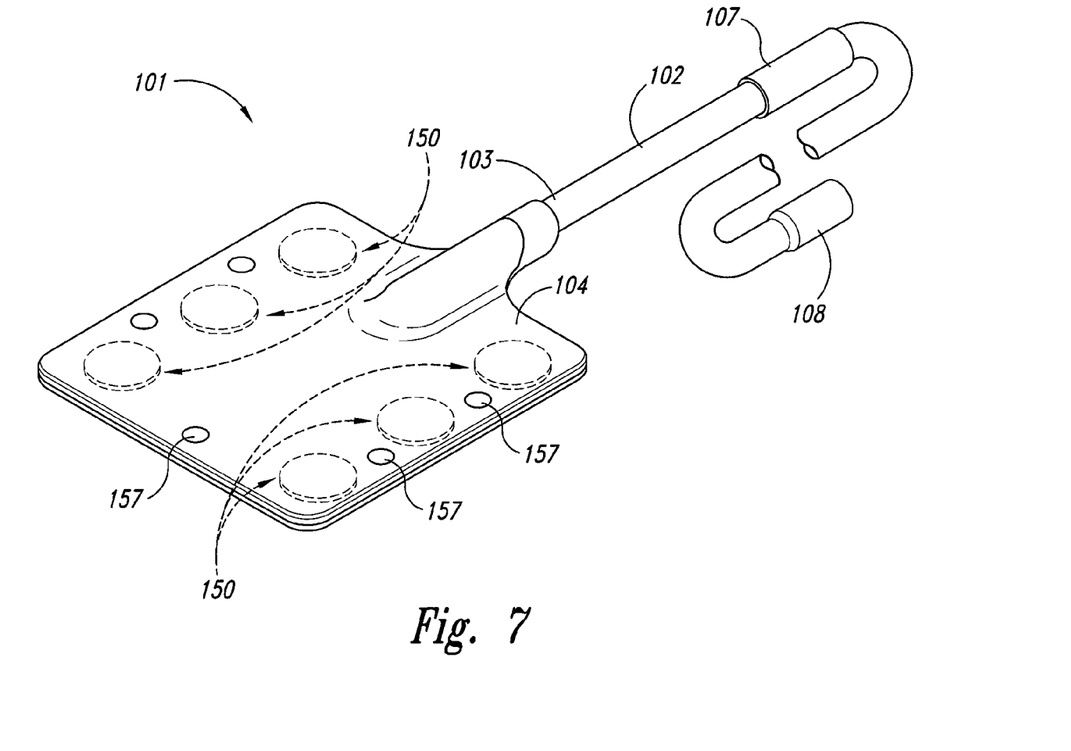
FIG. 7 is an isometric view of a signal delivery device that carries electrodes in accordance with an embodiment of the invention.

As described above with reference to FIG. 3, the target signal delivery areas can include areas in a cortical region 130 and/or in a subcortical region 131. Accordingly, the signals delivery device 101 selected for providing electromagnetic signals can include provisions for signal delivery to cortical and/or subcortical regions, depending on the patient's condition. FIG. 7 is a top, partially hidden isometric view of an embodiment of the signal delivery device 101 described above configured to carry multiple cortical electrodes 150. The electrodes 150 can be carried by a flexible support member 104 to place each electrode 150 in contact with a target site of the patient when the support member 104 is implanted. Electrical signals can be transmitted to the electrodes 150 via leads carried in the communication link 103. The communication link 103 can include a cable 102 that is connected to the pulse system 110 (FIG. 6) via a connector 108, and is protected with a protective sleeve 107. Coupling apertures or holes 157 can facilitate temporary attachment of the signal delivery device 101 to the dura mater at, or at least proximate to, a target signal delivery site. The electrodes 150 can be biased cathodally and/or anodally, as described above. In an embodiment shown in FIG. 7, the signal delivery device 101 can include six electrodes 150 arranged in a 2×3 electrode array (i.e., two rows of three electrodes each), and in other embodiments, the signal delivery device 101 can include more or fewer electrodes 150 arranged in symmetrical or asymmetrical arrays. The particular arrangement of electrodes 150 can be selected based on the region of the patient's brain that is to receive electromagnetic signals, and/or the patient's condition.

Figure 8A:
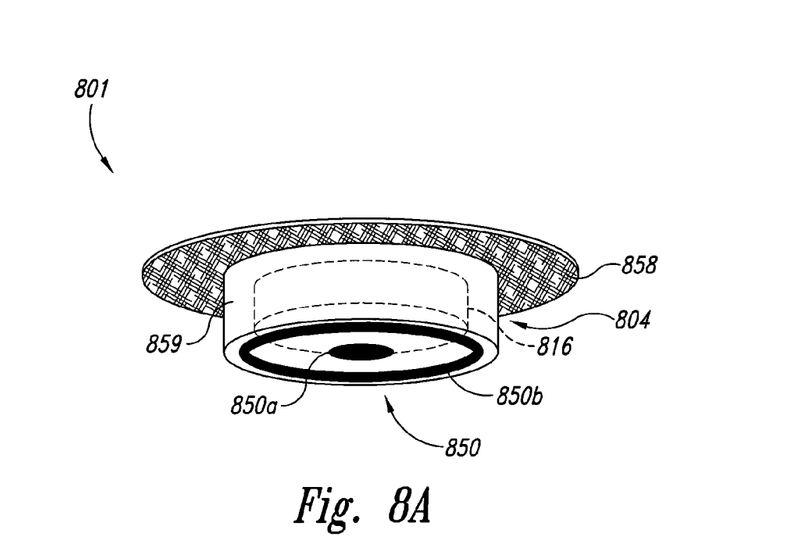
FIGS. 8A-8B illustrate a signal delivery device configured to be carried by the patient's skull in accordance with an embodiment of the invention.
Figure 8B:
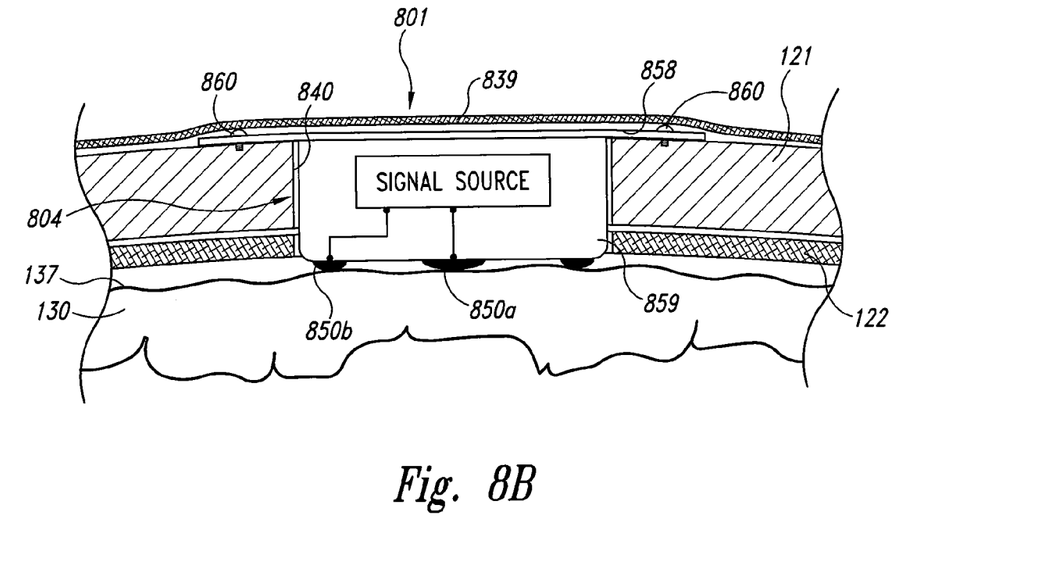

FIGS. 8A and 8B are isometric and cross-sectional views, respectively, of a signal delivery device 801 configured to apply signals to a region of the cortex proximate to the pial surface. Referring first to FIG. 8A, the signal delivery device 801 can include first and second electrodes 850 (identified individually by reference numbers 850a and 850b) and can be integrated with a pulse generator 816 (shown schematically), all of which are carried by a support member 804. The support member 804 can be configured to be implanted into the skull or another intracranial region of the patient. For example, the support member 804 can include a housing 859 and an attachment element 858 connected to the housing 859. The housing 859 can be a molded casing formed from a biocompatible material that has an interior cavity carrying the pulse generator 816. The attachment element 858 can be used to secure the housing 859 in position.

Referring now to FIG. 8B, the signal delivery device 801 is implanted into the patient by forming an opening in the patient's scalp 839, and cutting a hole 840 through the skull 121 and through the dura mater 122. The hole 840 should be sized to receive the housing 859, and in most applications, the hole 840 should be smaller than the attachment element 858. A practitioner inserts the housing 859 into the hole 840 and secures the attachment element 858 to the skull 121. The attachment element 858 can be secured to the skull 121 using a plurality of fasteners 860 (e.g., screws, spikes, etc.) or an adhesive. Once implanted, the electrodes 850a, 850b contact and/or optionally press against a desired portion of the brain at the target site. For example, the electrodes 850a, 850b can contact and press against the pia mater 137 surrounding the cortex 130.

Figure 9:
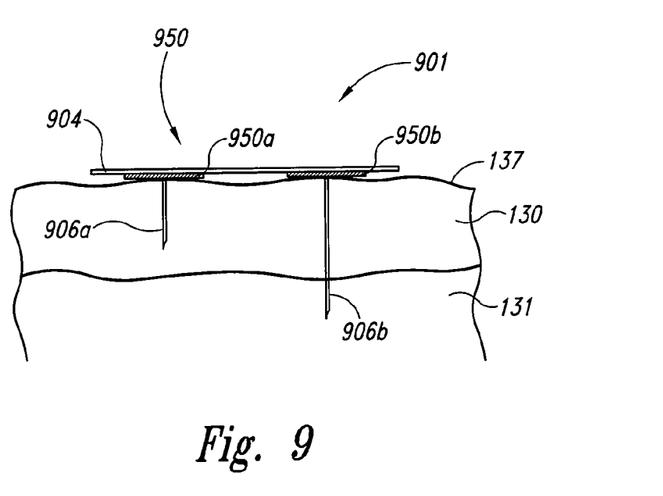
FIG. 9 illustrates a signal delivery device having electrodes configured to deliver electromagnetic signals to cortical and subcortical regions in accordance with an embodiment of the invention.

FIG. 9 is a side elevational view of a signal delivery device 901 configured to apply signals to cortical and/or subcortical tissue in accordance with another embodiment of the invention. The signal delivery device 901 includes multiple electrodes 950, two of which are shown in FIG. 9 as a first electrode 950a and a second electrode 950b. The electrodes 950 also include first and second electrically conductive pins 906a and 906b. The pins 906a, 906b can be configured to extend below the pial surface of the cortex. For example, because the length of the first pin 906a is less than the thickness of the cortex 130, the tip of the first pin 906a will accordingly conduct the electrical pulses to a stimulation site within the cortex 130 below the pial surface.

The length of the second pin 906b is greater than the thickness of the cortex 130 to conduct the electrical pulses to a portion of the brain below the cortex 130, e.g., the subcortex 131. The lengths of both pins can be selected to conduct the electrical pulses to target sites below the pia mater 137. As such, the lengths of the pins 906a, 906b can be the same for each electrode 950 or different for individual electrodes 950. Additionally, only a selected portion of the electrodes 950 and the pins 906 can have an exposed conductive area. For example, the electrode 950 and a portion of the pins 906 can be covered with a dielectric material so that the only exposed conductive material is at the tips of the pins 906. It will be appreciated that any of the electrode configurations described above can apply an electrical current to target sites below the pia mater by providing pin-like electrodes in a manner similar to that shown in FIG. 9A.

Figure 10:
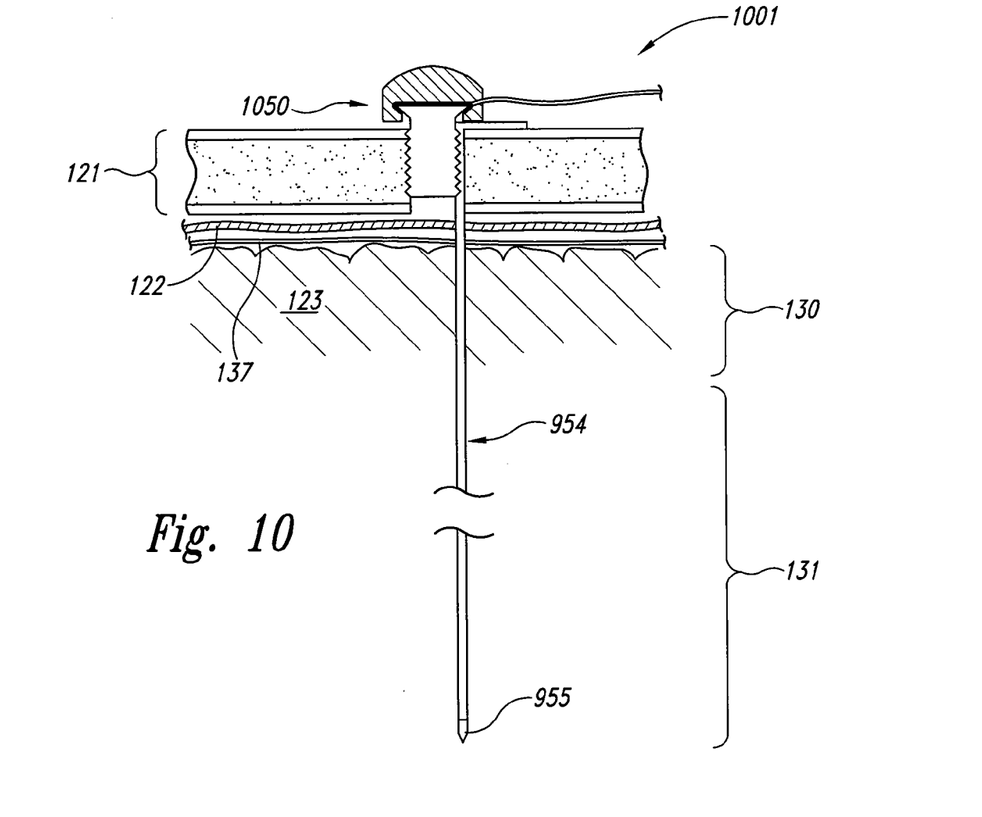
FIG. 10 is a side elevation view of an electrode configured to deliver electromagnetic signals to a subcortical region in accordance with an embodiment of the invention.

FIG. 10 illustrates a signal delivery device 1001 that may be configured to apply electrical signals to the cortical region 130 or the subcortical region 131 in accordance with another embodiment of the invention. The signal delivery device 1001 can include an electrode 1050 having a head and a threaded shaft that extends through a pilot hole in the patient's skull 121. If the electrode 1050 is intended for cortical signal delivery, it can extend through the skull 121 to contact the dura mater 122 or the pia mater 137. If the electrode 950 is to be used for subcortical signal delivery, it can include an elongate conductive member 954 that extends downwardly through the cortical region 130 into the subcortical region 131. Most of the length of the elongate conductive member can be insulated, with just a tip 955 exposed to provide electrical stimulation in only the subcortical region 131. Further details of devices that may be suitable for electromagnetic signal delivery in accordance with other embodiments of the invention are described in the following published U.S. Applications/issued patents, all of which are incorporated herein by reference: 2005/0075680-A1; 2004/0102828-A1; and U.S. Pat. No. 7,010,351.

Figure 11:
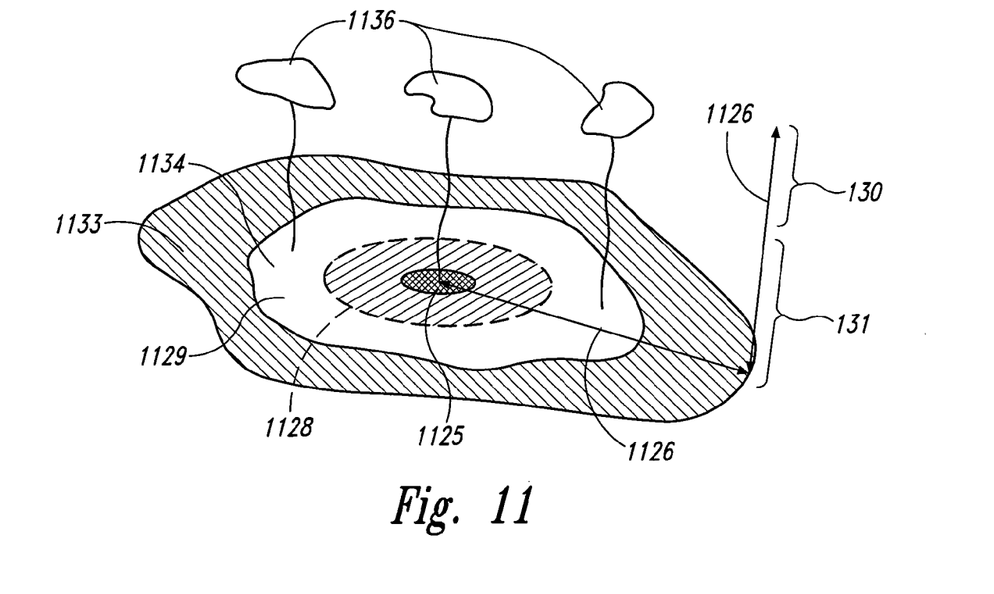
FIG. 11 is a partially schematic illustration of an infarct region and affected region in a subcortical area of the brain.

D. Further Examples of Target Signal Delivery Site Selection and Associated Methods As discussed above with reference to FIG. 3, a stroke or other lesion in the cortical region can affect cortical tissue and/or subcortical tissue. In other embodiments, a stroke or other lesion in the subcortical region can affect cortical and/or subcortical tissue. For example, as shown schematically in FIG. 11, a dysfunctional region 1125 can be located in the subcortical region 131 and can be surrounded by an affected region 1126. The affected region 1126 can extend laterally within the subcortical region 131 and can extend outwardly into the cortical region 130. Accordingly, cortical structures 1136 can also be included in the affected region 1126. The affected region 1126 can contain high morbidity tissue 1128, low morbidity tissue 1129, hypoactive tissue 1134, and hyperactive tissue 1133, any of which can be located in the cortical region 130 and/or the subcortical region 131. Cortical and/or subcortical electrodes can be implanted in the affected region 1126 to direct signals to appropriate neural structures. The appropriate neural structure can be determined using methods generally similar to those described previously.

Figure 12:
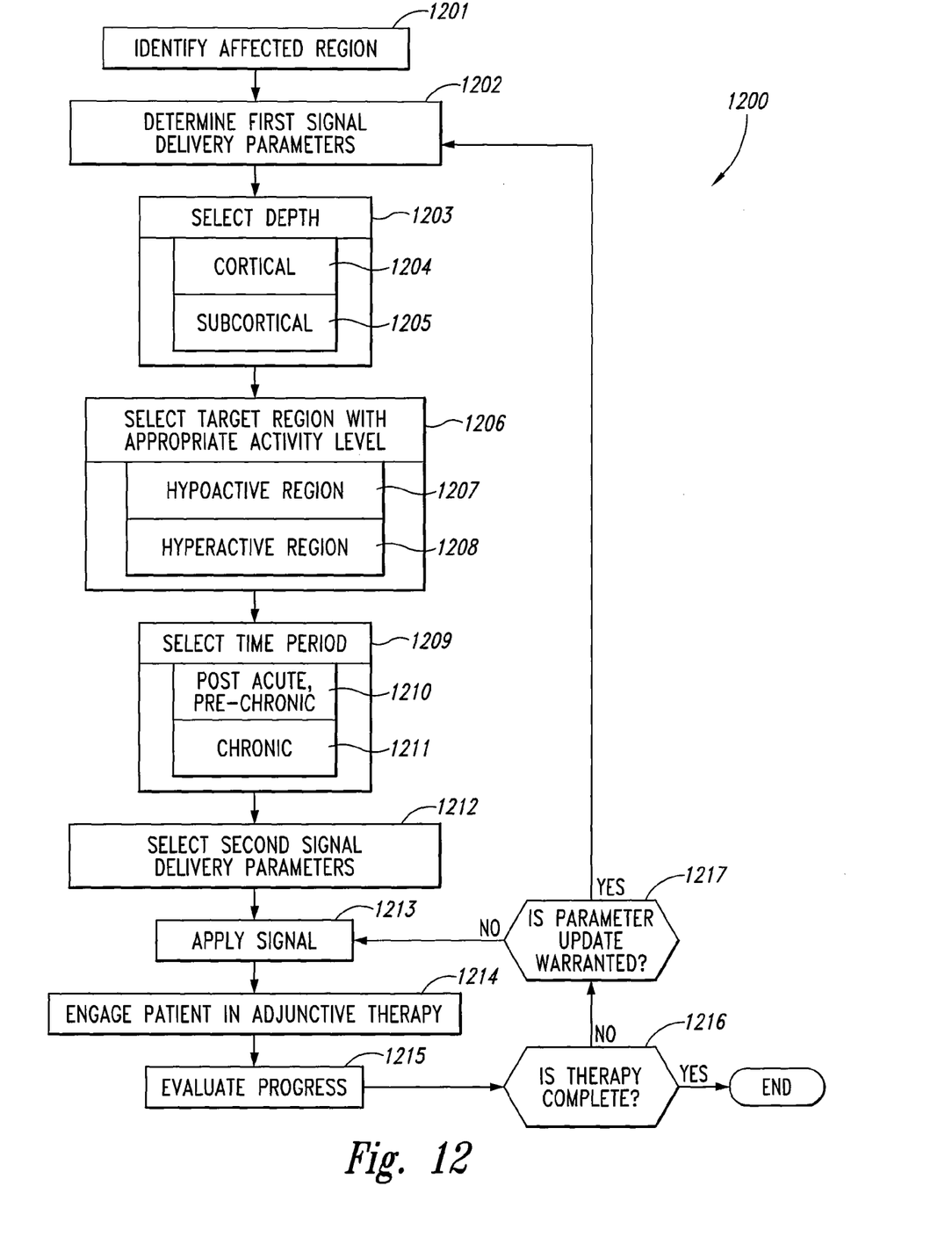
FIG. 12 is a flow diagram illustrating a process for carrying out a treatment regimen that includes electromagnetic signals in accordance with an embodiment of the invention.

FIG. 12 is a flow diagram illustrating a method 1200 for applying signals (e.g., extrinsic, electromagnetic signals) to neural tissue in accordance with an embodiment of the invention. In process portion 1201, the process 1200 can include identifying an affected region, e.g., a region including neuronal tissue that, at least during a pre-dysfunctional period, was in neural communication with neuronal tissue in a dysfunctional region. As described above, the affected region (and in particular, a target neural population within the affected region) can be identified generally by proximity to the dysfunctional region, and/or more particularly using analytical techniques, including but not limited to diffusion tensor imaging. The use of diffusion tensor imaging can lead the practitioner to identify tracts that are damaged or lesioned, as well as tracts that are expected to be viable or healthy. Accordingly, the practitioner may elect not to apply signals to sites that otherwise would receive signals, based on an indication that the tracts associated with such sites are damaged. Conversely, the practitioner may identify sites that otherwise would not receive signals, based on an indication that such sites are in communication with intact tracts. In still further embodiments, as discussed above, the practitioner may apply signals to tissue that was in communication with the dysfunctional region prior to the dysfunction, even if tracts to the dysfunctional region are damaged, so long as alternative viable tracts remain. Also, the practitioner may also select particular neural regions to receive electromagnetic stimulation based upon viable tract density.

In process portion 1202, the process can include determining any of several first signal delivery parameters prior to implanting a signal delivery device and delivering corresponding electromagnetic signals. For example, in process portion 1203, the depth at which the signals are provided can be selected. This can include selecting a cortical depth (process portion 1204) and/or a subcortical depth (process portion 1205). At least one target region that is to receive the signals can also be selected, where the selection can be based at least in part on its activity level (process portion 1206). For example, a target region having a hypoactive neural response level can be selected (process portion 1207). In other embodiments, a target region having (at least initially) hyperactive neural activity levels can be selected (process portion 1208). As described above, such regions may be selected to receive inhibitory signals (or no excitatory signals) initially, and then receive excitatory signals after the neural activity level has dropped to an appropriate level.

In still a further aspect of an embodiment shown in FIG. 12, the time period(s) during which signals are applied can also be selected (process portion 1209). For example, the practitioner can select a post-acute, pre-chronic period during which to apply the signals (process portion 1210). If the signals provided during the post-acute, pre-chronic period are sufficient to achieve the desired level of patient recovery, then in at least one embodiment no further signals need be provided. Alternatively, signals can be provided during one or more portions of a chronic period (process portion 1211) in addition to or in lieu of providing signals during the pre-chronic period.

As used herein, the term "post-acute, pre-chronic period" refers generally to the time period following a lesion event (or other event that triggers and/or is associated with the onset of a dysfunction), during which functional degradation resulting from the lesion is still occurring, and/or during which the body's natural recovery response to the lesion is still on-going. One measure of the onset of this period may be when inflammation associated with the lesion has subsided, which may also present a reasonable opportunity for implanting an electromagnetic signal delivery device. An indication of the end of this period can include a plateau in patient recovery, identified for example, by a failure to further improve performance of a physical task (e.g., ADL).

The chronic period refers generally to the period following the post-acute, pre-chronic period (e.g., after additional functional degradation resulting from the lesion has ceased, and/or the body's natural recovery response has ceased). The initiation and duration of each time period can vary, depending upon such factors as the type of lesion suffered by the patient and/or the individual characteristics of the patient. For example, in some stroke cases, the post-acute, pre-chronic phase can began about two weeks after the stroke, and can last until 6-12 weeks post-stroke. The chronic phase can begin 6-12 weeks post-stroke and can continue indefinitely, although signal delivery may be halted or interrupted once the expected benefits have been achieved and solidified (e.g., 18 or more weeks post-stroke) or a functional performance plateau has been reached. In some embodiments, the chronic phase may include multiple electromagnetic stimulation periods, where such periods may be separated by a given number of days, weeks, or months (e.g., 4 weeks, or 3-6 months). Moreover, in particular embodiments, the chronic phase may involve the delivery of electromagnetic stimulation by way of multiple types of devices (e.g., implanted or transcranial cortical stimulation devices, deep brain stimulation devices, spinal column stimulation devices, or peripheral nerve stimulation devices), either within any given electromagnetic stimulation period or from one electromagnetic stimulation period to another.

In other embodiments, the foregoing time periods may have other values. In at least some embodiments, it may be advantageous to provide signals during the post-acute, pre-chronic period because during this period, such signals can supplement the patient's naturally occurring recovery mechanisms. The delineation or approximate delineation between the chronic phase and the post-acute, pre-chronic phase can be determined based on historical data for similarly situated patients, or based on data applicable to the individual patient at hand. Suitable techniques for determining data at a patient-specific level, or as part of an information collection effort for similarly situated patients can include (a) detecting physiologic markers (e.g., neural growth factors and/or cytokines in the patient's cerebrospinal fluid), (b) detecting contrast agents using imaging techniques (e.g., detecting a contrast agent that labels GABA receptors using a PET scan), and/or (c) measuring electrical signal via EEG and/or ECoG techniques.

One or more of several aspects of the treatment regimen can be different during the post-acute, pre-chronic period than during the chronic period. For example, the patient may receive adjunctive therapy (described further below) during the chronic period, but not during the post-acute, pre-chronic period. Certain signal delivery parameters, discussed further below, may also differ between the two periods.

In process portion 1212, second signal delivery parameters can be selected. Such parameters include signal frequency, voltage, current and other parameters. In addition to selecting the level of signals (e.g., the intensity or amplitude of suprathreshold stimulation and/or subthreshold stimulation), process portion 1212 can include selecting the manner by which the signal varies. The signal can include bi-phasic and/or mono-phasic pulses, varying in a periodic and/or an aperiodic (e.g., random or pseudorandom) manner.

The second signal delivery parameters can be selected based on any or all of the first signal delivery parameters. For example, the second signal delivery parameters may be different for delivery during the chronic period than for delivery during the post-acute, pre-chronic period. The second signal delivery parameters selected for signals provided to a previously or presently hypoactive region may be different than those selected for delivery to a previously or presently hyperactive region.

In process portion 1213, the electromagnetic signal is applied to the patient, and in process portion 1214, an optional adjunctive therapy is administered to the patient. The adjunctive therapy can form a portion of the overall treatment regimen, and may or may not be conducted simultaneously with the administration of electromagnetic signals to the target neural population. For example, the patient may undergo a treatment session during which electromagnetic signals are applied to the target neural population, and may subsequently undergo an adjunctive therapy session that can include a motor task (e.g., a speech task, or motion of a limb), administration of drugs, and/or other type of adjunctive treatment. Of course, in some embodiments, the patient can engage in adjunctive therapy simultaneously with receiving electromagnetic signals.

In process portion 1215, the progress of the foregoing signal delivery program is evaluated. If it is determined in process portion 1216 that the therapy is sufficient or complete (e.g., if it is determined that no significant additional benefit may be achieved with the therapy, or a given amount of time has elapsed, or a functional plateau has occurred), then the process can end. Otherwise, in process portion 1217, the process can include determining whether a parameter update is warranted. If so, the process can return to process portion 1202 to identify parameter updates that may continue, enhance, and/or solidify the benefits realized by the patient during the foregoing therapy.

Process portion 1215 can be carried out at one or more points during an overall treatment regimen. For example, process portion 1215 can be performed at one or more times during the post-acute, pre-chronic period to determine how effective the treatment is. If it is determined that the treatment effectiveness can be increased, any of the foregoing parameters (e.g., signal delivery location, strength, frequency, etc.) can be changed. Because the patient's own responses to the initial damage (or other event associated with the onset of a dysfunction) are still active during this period, it is quite likely that the signal delivery parameters may change more than once during this period. Signal delivery parameters may also change during the chronic period, though in at least some cases, not as often as during the pre-chronic period.

In particular embodiments, at least some of the process portions described above with reference to FIG. 12 can be automated, for example, in the context of computer-based instructions that may be resident on computer-readable media. The computer-readable media (or aspects thereof) can be included in the devices described above, and/or in separate units. In a particular embodiment shown schematically in FIG. 13, such a computer-readable medium 1310 can include a receiver portion 1302 that is configured to receive information corresponding to neuronal structures and/or functions. In general, the information includes physiologic information, or physiologic correlate information corresponding to the neuronal state of neuronal tissue. Physiologic information refers generally to directly measured information, e.g., the measured electrical activity level of a neuronal population. Physiologic correlate information refers generally to information that is correlated with neuronal state, but may not be a direct measure of neuronal state, e.g., blood oxygen levels of a neuronal population, or an EEG-related coherence measurement. The receiver portion 1302 can receive first information 1305 that includes neuronal structure and/or chemical information. Such information is available via MRI techniques, diffusion tensor imaging techniques, and/or other techniques. The receiver portion 1302 can receive second information 1306 in addition to or in lieu of the first information, with the second information 1306 including neural function and/or activity level information. Such information is available via fMRI techniques, EEG techniques, ECoG techniques, and/or other techniques.

Figure 13:
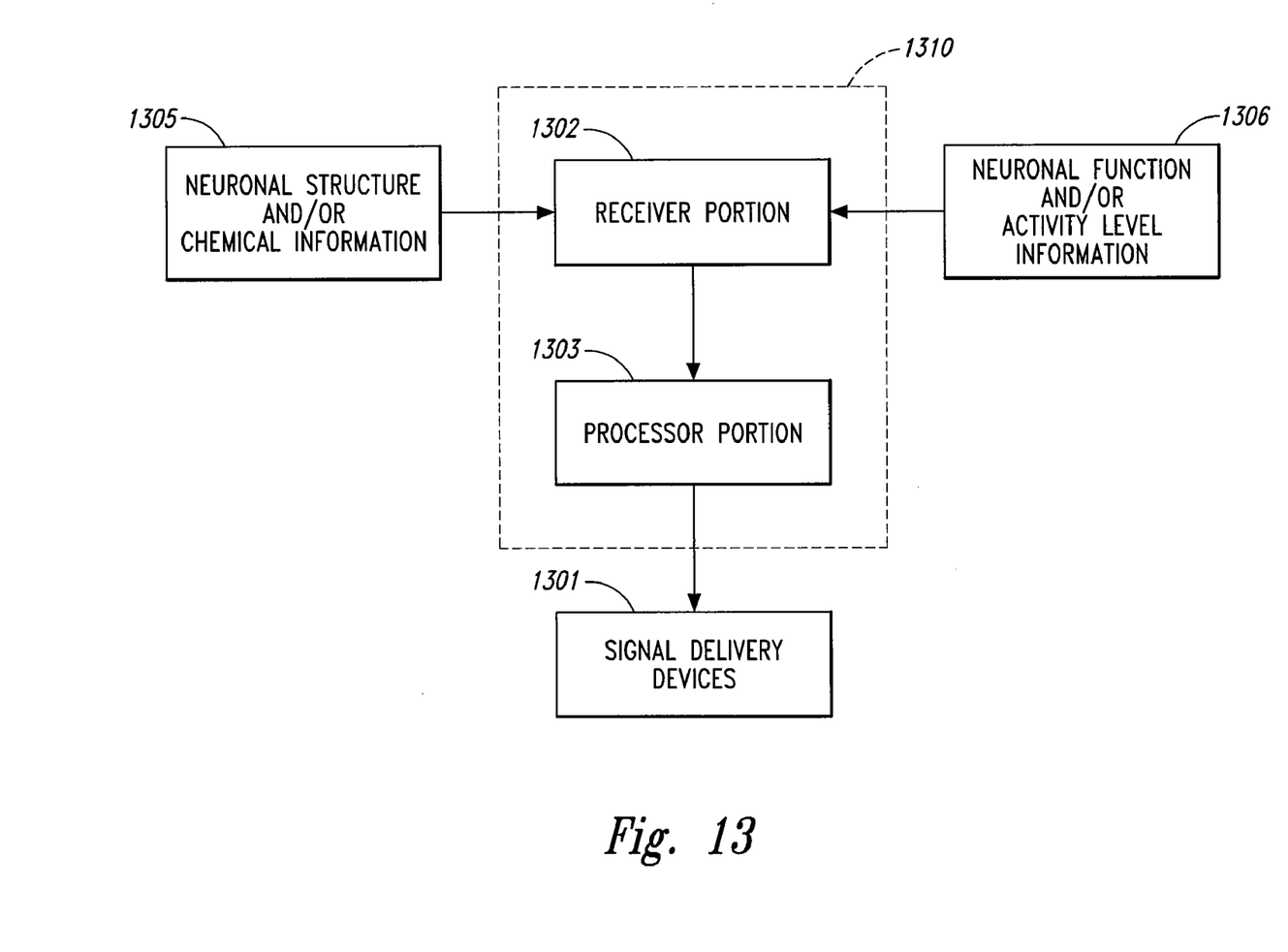
FIG. 13 is a block diagram illustrating components of a computer-based system in accordance with an embodiment of the invention.

The computer-readable medium 1310 can further include a processor portion 1303 that is coupled to the receiver portion 1302 and is configured to identify neuronal tissue at an affected region. As described above, the affected region can include neuronal tissue that, at least during a pre-dysfunction period, was in neural communication with neuronal tissue in a corresponding dysfunctional region. The processor portion 1303 can further be configured to select a neural signal delivery site at the affected region based at least in part on the information received by the receiver portion 1302. Accordingly, a computer-readable medium 1310 having the foregoing characteristics can automatically select signal delivery sites based on information received using imaging or other techniques, with or without user intervention. One or more signal delivery devices 1301 can then be used to direct signals to the signal delivery site(s).

As described above, the computer-readable medium 1310 can include a receiver portion 1302 configured to receive information corresponding to activity levels of neuronal structures. For example, the activity levels can include the hypoactive activity levels and/or the hyperactive activity levels described above with reference to FIG. 3. The processor portion 1303 can be configured to distinguish between hyperactive activity levels and hypoactive activity levels, e.g., by comparing the actual activity levels with normal or otherwise expected activity levels. The processor portion 1303 can further be operatively coupleable to the signal delivery device 1301 to direct electrical current to neuronal tissue based at least in part on information received from the receiver portion 1302. Accordingly, the processor portion 1303 can be configured to direct electrical current preferentially to electrodes (or other signal delivery elements) positioned proximate to neuronal structures exhibiting hypoactive activity levels. In other embodiments, the processor portion 1303 can be configured to shunt electrical current from electrodes positioned proximate to neuronal structures exhibiting hyperactive activity levels to electrodes positioned proximate to neuronal structures exhibiting hypoactive activity levels. In still further embodiments, the processor portion 1303 can be configured to direct inhibitory signals to the hyperactive neuronal structure.

In still another embodiment, the receiver portion 1302 of the computer-readable medium 1310 can be configured to receive multiple segments of information corresponding to at least one characteristic of neuronal structures obtained at multiple points in time. The processor portion 1303 can be configured to identify when the neuronal structures achieve a steady state or a more normal or improved state based at least in part on the multiple segments of information. For example, the processor portion 1303 can be configured to identify when a performance level of the neuronal structure (measured in some cases by patient tests) levels off or otherwise ceases to show further improvement. In a particular example, the computer-readable medium 1310 can automatically receive performance data (e.g., performance of a physical, computer-based task) and can automatically determine when the rate of improvement falls below a threshold rate. At this point, the computer-readable medium 1310 can alert a practitioner, and/or automatically terminate a signal delivery regimen.

One feature of several embodiments of the systems and methods described above is that they can include identifying and directing signals to neuronal tissue that has been affected by a lesion or other event associated with a dysfunction, but may not necessarily be directly damaged by the lesion. Instead, the effect may include a loss of communication with the dysfunctional region. It is believed that providing electromagnetic signals to this tissue may, in at least some cases, at least partially offset the tendency for cells in this region to atrophy or otherwise degrade as a result of the loss of communication with the infarcted region. Accordingly, an advantage of this feature is that it can counteract at least some of the potential damage due to the dysfunction. It is expected that in some embodiments, the electromagnetic signals can result in restoration and/or repair of existing neuronal pathways, and that in other embodiments, the electromagnetic signals can result in the formation of new neuronal pathways. Either or both type of improvement may occur in any given patient.

The foregoing techniques can be used to avoid applying signals to areas that may be unrecoverable, and/or identify areas that may be recoverable, but may appear inactive or dead. These techniques can also be used to distinguish among potentially recoverable areas. For example, these techniques can be used to distinguish altered areas that have more or more robust fiber tracts (e.g., higher quality, and/or greater integrity tracts) from those that do not. In some cases, patients may be excluded if they have insufficient tracts with sufficient integrity.

The analysis of tracts (e.g., using DTI) can be combined with other imaging techniques to identify appropriate signal delivery sites. For example, MRI can be used to identify a particular area of interest (e.g., a particular brain structure, including but not limited to a peri-infarct, affected brain structure), and DTI can be used to assess the viability of tracts that connect with the area of interest. The practitioner can then elect to target portions of the general area that have robust tracts and/or areas that have less robust (e.g., less dense tracts). In at least some cases, applying signals to areas having robust tracts can encourage additional activity in these areas and/or in other areas that communicate with these areas via the tracts. In at least some cases, applying signals to areas with less robust tracts can forestall or prevent degeneration of these areas. Different stimulation periods or stimulation parameters may be specified based upon tract characteristics. For example, an area having more viable tracts may be stimulated at approximately 50% of a patient response threshold (e.g., a movement or sensation threshold), while an area having fewer viable tracts may be stimulated at approximately 75% of a patient response threshold. During the course of treatment, these techniques can be repeated to identify migration of activity from one tract or set of tracts to another. The signal delivery parameters (including signal delivery location) can be selected, varied, or updated accordingly.

In another embodiment, tract analysis can be used in conjunction with fMRI. For example, fMRI techniques can be used to identify a functionally active area of the brain, which may include an affected region and other regions as well. Tractography can then be used to identify, with significantly increased granularity, the tracts associated with different parts of the active area. As discussed above, the practitioner can elect to deliver signals to those parts of the active area that have at least some viable tracts, but may be at risk of degeneration due to a loss of tracts. The practitioner can avoid areas that have no viable tracts, and as discussed above, and can elect to deliver signals to areas with robust tracts if it is expected that doing so will achieve effective results.

In other embodiments, tract analysis can be used to guide the selection of a signal delivery device location without the use of fMRI or another neurofunctional localization procedure. For example, if the patient has suffered damage to the region of the cortex responsible for hand motion, then tractography techniques can be used to trace tracts from the mid-brain peduncle associated with this motion. This in turn will identify other brain areas (at the cortex or elsewhere) that may be suitable for receiving electromagnetic signals. The target areas may be selected based on factors that include, but are not limited to, tract robustness, as discussed above. Particular target areas may be located at portions of the motor cortex other than the damaged region, at other motor-related areas (e.g., the SMA, pre-motor area, post-central gyrus, cingulate motor gyrus and/or contralateral gyri), or other areas such as the somatosensory cortex.

In particular embodiments, the applied signals can benefit the neural communication to and/or from a target neural population in the affected region, and/or the applied signals can improve the functionality of the target neural population. For example, signals applied in accordance with a first set of parameters can at least reduce (if not halt) a loss of neural signal communication to and/or from the target neural population. Such applied signals can also reduce the loss of cells in this region. In a particular embodiment, the first set of signal delivery parameters can include anodal signals, which tends to penetrate relatively deeply into the neuronal tissue and tends to affect the cell body's ability to generate action potentials. Conversely, delivery signals in accordance with a second set of parameters can include cathodal signal delivery, which tends to affect the neuroplastic characteristics of neuronal cell dendrites, which in turn can improve functionality of the target population via neuroplastic adaptation. Signal application with the first set of parameters can precede signal application with the second set of parameters to initially reduce cell loss, after which subsequent signal application with the second set of parameters can improve cell functionality.

Another feature of embodiments of the systems and methods described above is that they can include distinguishing between tissue that (as a result of a dysfunction event), may nevertheless be likely to survive, from tissue that (as a result of the dysfunction event), is likely to die. An advantage of this feature is that it can allow the practitioner to focus the applied signals on regions that are most likely to benefit from such signals and can accordingly provide a more efficient way of improving the patient's functioning level.

Still another feature of embodiments of the systems and methods described above is that they can include distinguishing between hypoactive neuronal tissue and hyperactive neuronal tissue, and can further include selectively or preferentially applying electromagnetic signals to the hypoactive regions. An advantage of this feature is that it can improve the efficiency of a signal delivery program by directing the signals to the tissue most likely to benefit from such signals, while not applying signals to tissue that may already be stimulated (and perhaps over-stimulated) as a result of the patient's natural response to a dysfunctional event.

Still another feature of embodiments of the systems and methods described above is that they can include applying signals during a post-acute, pre-chronic period following a lesion or other dysfunction event. This may have several benefits, including supplementing or beneficially modulating the patient's naturally occurring rehabilitative responses to a dysfunction event. In addition, electromagnetic signals applied during this period may be applied for a longer period and/or may have a longer lasting effect than the existing application of drugs to the patient during this period. Accordingly, this technique can improve and/or enhance the patient's recovery in response to an infarct or other damage or degradation.

Still another feature of systems and methods described above is that they can include identifying target neural populations by identifying the existence of, location of, and/or health of tracts or other projections that are coupled to the target signal delivery area and/or the dysfunctional area. For example, diffusion tensor imaging can be used to provide the foregoing assessments. Based on the results of such assessments, a practitioner can identify target signal delivery sites with a greater level of confidence that signals applied at these areas will result in an improvement for the patient.

From the foregoing, it will be appreciated that specific embodiments of the invention have been described herein for purposes of illustration, but that various modifications may be made without deviating from the invention. For example, many of the techniques described above for applying electromagnetic signals include applying a varying electrical signal via one or more implanted electrodes. In other embodiments, suitable electromagnetic signals can be provided by transcranial magnetic stimulation (TMS) and/or transcranial direct current stimulation (tDCS). Furthermore, while the devices described above were described in the context of cortical and/or subcortical (e.g., deep brain) devices, the signals may be provided to other neural populations in other embodiments. Such neural populations can be located at the cerebellum, medulla, and/or spinal cord. Aspects of the invention described in the context of particular embodiments may be combined or eliminated in other embodiments. Further, while advantages associated with certain embodiments of the invention have been described in the context of those embodiments, other embodiments may also exhibit such advantages, and not all embodiments need necessarily exhibit such advantages to fall within the scope of the invention. Accordingly, the invention is not limited except as by the appended claims.

We claim:

1. A method for treating neuronal tissue of a patient using electrical stimulation, comprising:
   identifying a location of an infarct region having dysfunctional neuronal tissue that was subjected to a reduced oxygen supply;
   based at least in part on the location of the infarct region, identifying an affected region having low morbidity tissue, the affected region including neuronal tissue that, at least during a pre-infarct period, was in neural communication with the dysfunctional neuronal tissue in the infarct region, wherein neuronal tissue in the affected region has reduced neural signal transmission as a result of tissue loss at the infarct region;
   implanting at least one electrode at least on, near or adjacent the affected region;
   selecting a first set of stimulation parameters such that the neuronal tissue in the affected region is stimulated during a post-acute, pre-chronic period relative to the onset of damage to the low-morbidity neuronal tissue in the affected region; and
   selecting a second set of stimulation parameters such that the neuronal tissue in the affected region is stimulated during a chronic period once the onset of damage to the low-morbidity neuronal tissue has occurred; and
   controlling a pulse generator to generate electrical pulses and to apply electrical pulses to the patient through the electrode according to the first and second set of stimulation parameters.

2. The method of claim 1 further comprising directing the patient to engage in adjunctive therapy during the chronic period.

3. The method of claim 1 wherein the post-acute, pre-chronic period comprises the period of approximately two weeks after the infarct to about 6 to 12 weeks post-infarct.

4. The method of claim 1 wherein identifying the affected region includes using a diffusion tensor imaging technique.

5. The method of claim 1 wherein the dysfunctional region is a cortical region and wherein identifying the affected region includes identifying a subcortical affected region.

6. The method of claim 1 wherein the dysfunctional region is subcortical region and wherein identifying the affected region includes identifying a cortical affected region.

7. The method of claim 1 further comprising not applying electrical signals to neuronal cells of the affected region having hyperactive spontaneous electrical activity levels.

8. The method of claim 1 further comprising preferentially applying electrical signals to neuronal cells of the affected region having hypoactive spontaneous electrical activity levels.

9. The method of claim 1 further comprising:
   preferentially applying electrical signals to first neuronal cells of the affected region having hypoactive spontaneous electrical activity levels;
   not applying electrical signals to second neuronal cells of the affected region having hyperactive spontaneous electrical activity levels; and
   after spontaneous electrical activity levels of the second neuronal cells become hypoactive, applying electrical signals to the second neuronal cells.

10. The method of claim 1 further comprising:
    re-evaluating neural activity of the affected region after the electrical signals via the first set of stimulation parameters;
    detecting a shift in the neural activity; and
    updating at least one parameter in the first set of stimulation parameters.

11. The method of claim 1 further comprising:
    re-evaluating neural activity of the affected region after the electrical signals via the second set of stimulation parameters;
    detecting a shift in the neural activity; and
    updating at least one parameter in the second set of stimulation parameters.

12. The method of claim 1 wherein the electrodes of an electrode array are positioned on or in the low morbidity tissue region.

13. A method for treating neuronal tissue of a patient using electrical stimulation, comprising:
    identifying a location of an infarct region having dysfunctional neuronal tissue that was subjected to a reduced oxygen supply;
    based at least in part on the location of the infarct region, identifying an affected region having low morbidity tissue, the affected region including neuronal tissue that, at least during a pre-infarct period, was in neural communication with the dysfunctional neuronal tissue in the infarct region, wherein neuronal tissue in the affected region has reduced neural signal transmission as a result of tissue loss at the infarct region;
    positioning at least one electrode at least on, near or adjacent the affected region;
    controlling a pulse generator to generate electrical pulses and to apply electrical pulses to the patient through the electrode according to a set of stimulation parameters comprising a first set of stimulation parameters such that the neuronal tissue in the affected region is stimulated during a post-acute, pre-chronic period relative to the onset of damage to the low-morbidity neuronal tissue in the affected region; a second set of stimulation parameters such that the neuronal tissue in the affected region is stimulated during a chronic period once the onset of damage to the low-morbidity neuronal tissue has occurred or a combination of the first and second set of stimulation parameters;
    identifying the onset of a chronic period relative to the occurrence of damage to the neuronal tissue; and
    directing the patient to engage in adjunctive therapy during the chronic period.

* * * * *